US010197546B2

(12) United States Patent
Rahaliou et al.

(10) Patent No.: US 10,197,546 B2
(45) Date of Patent: Feb. 5, 2019

(54) METHOD AND SYSTEM FOR CONTINUOUS MONITORING OF THE WATER FRACTION IN AN OIL WELL STREAM

(71) Applicants: Aleksander Rahaliou, Minsk (BY); Aliaksander Chakhouski, Minsk (BY); Aliaksei Sottsau, Minsk (BY); Ramir Akbashev, Moscow (RU); Sergei Orel, Moscow (RU)

(72) Inventors: Aleksander Rahaliou, Minsk (BY); Aliaksander Chakhouski, Minsk (BY); Aliaksei Sottsau, Minsk (BY); Ramir Akbashev, Moscow (RU); Sergei Orel, Moscow (RU)

(73) Assignee: Sergei Piltsov, Lytkarino (RU)

( * ) Notice: Subject to any disclaimer, the term of this patent is extended or adjusted under 35 U.S.C. 154(b) by 216 days.

(21) Appl. No.: 15/373,463

(22) Filed: Dec. 9, 2016

(65) Prior Publication Data
US 2018/0163537 A1 Jun. 14, 2018

(51) Int. Cl.
*G01N 33/28* (2006.01)
*G01N 27/02* (2006.01)
(Continued)

(52) U.S. Cl.
CPC ......... *G01N 33/2823* (2013.01); *E21B 47/10* (2013.01); *G01N 27/026* (2013.01); *G01N 33/2847* (2013.01); *E21B 2049/085* (2013.01)

(58) Field of Classification Search
CPC ... G01N 27/026; G01N 33/2847; E21B 47/10
See application file for complete search history.

(56) References Cited

U.S. PATENT DOCUMENTS 5,033,289 A 7/1991 Cox
5,287,752 A 2/1994 Den Boer
(Continued)

FOREIGN PATENT DOCUMENTS

CN 201689071 U 12/2010
CN 101865873 B 3/2013
(Continued)

OTHER PUBLICATIONS

Hammer, Erling, A, Capacitance Transducers—Basic Principles.
(Continued)

*Primary Examiner* — Jermele M Hollington
*Assistant Examiner* — Alvaro Fortich
(74) *Attorney, Agent, or Firm* — Michael E. Zall (57) ABSTRACT

A method, system and apparatus for continuously determining the watercut of production fluid flowing in a pipeline from an oil reservoir. The method includes providing an electrochemical impedance sensor at a fixed location in the pipeline for continuously measuring the impedance value of the flowing production fluid at such location. A sample of the production fluid is obtained from the pipeline to determine the watercut value of the sample. From such watercut values from the sample, a correlation formula is determined of the watercut value of the sample with the measured impedance value at the fixed location. Subsequently the continuously measured impedance values are inputted into the correlation formula to continuously calculate the watercut value of the flowing production fluid to thereby continuously determine the watercut of the flowing production fluid with the impedance sensor.

16 Claims, 10 Drawing Sheets

(51) Int. Cl.
*E21B 47/10* (2012.01)
*E21B 49/08* (2006.01)

(56) References Cited

U.S. PATENT DOCUMENTS

| | | | |
|---|---|---|---|
| 5,675,259 | A | 10/1997 | Arndt |
| 5,793,216 | A | 8/1998 | Constant |
| 6,076,049 | A | 6/2000 | Lievois et al. |
| 6,097,786 | A | 8/2000 | Groves et al. |
| 6,272,915 | B1 | 8/2001 | Kostelnicek et al. |
| 6,292,756 | B1 | 9/2001 | Lievois et al. |
| 6,318,156 | B1 | 11/2001 | Dutton et al. |
| 6,945,122 | B2 | 9/2005 | Foss et al. |
| 7,201,068 | B2 | 4/2007 | Foss et al. |
| 7,293,471 | B2 | 11/2007 | Lund Bø et al. |
| 8,505,363 | B2 | 8/2013 | Masek |
| 2004/0253735 | A1 | 12/2004 | Vadgama et al. |
| 2006/0247869 | A1 | 11/2006 | Lucero |
| 2008/0288181 | A1 | 11/2008 | Lucero |
| 2011/0146413 | A1 | 6/2011 | Masek |
| 2012/0017697 | A1 | 1/2012 | Benzo et al. |
| 2013/0035879 | A1* | 2/2013 | Nardi .......... G01F 1/74 702/50 |
| 2013/0110411 | A1 | 5/2013 | Black et al. |
| 2015/0083402 | A1 | 3/2015 | Manin |
| 2015/0308261 | A1* | 10/2015 | Zuo .......... E21B 49/08 166/250.01 |
| 2016/0245073 | A1* | 8/2016 | Hansen .......... E21B 43/00 |

FOREIGN PATENT DOCUMENTS

| | | |
|---|---|---|
| CN | 204374134 U | 6/2015 |
| CN | 104820000 A | 8/2015 |
| CN | 104989371 A | 10/2015 |
| KR | 100489813 B1 | 5/2005 |
| RU | 2063615 C1 | 7/1996 |
| RU | 59239 U1 | 12/2006 |
| RU | 2329471 C1 | 7/2008 |
| RU | 2334951 C1 | 9/2008 |
| RU | 2336500 C1 | 10/2008 |
| RU | 2397479 C1 | 8/2010 |
| RU | 104727 U1 | 5/2011 |
| RU | 2479036 C1 | 4/2013 |
| RU | 129256 U1 | 6/2013 |
| RU | 2484381 C1 | 6/2013 |
| RU | 2488109 C2 | 7/2013 |
| RU | 2498286 C1 | 11/2013 |
| RU | 2522316 C1 | 7/2014 |
| RU | 2571788 C1 | 12/2015 |

OTHER PUBLICATIONS

Zubair, Muhammad, A High Resolution Capacitive Sensing System for the Measurement of Water Content in Crude Oil; Sensors 2014, 14, 11351-11361. Published Jun. 25, 2014.

Rodriguez, Iara, H., Capacitive wire-mesh sensor Measurements in oil-water flow.

Erdogan, Burak, Watercut Measurement Method Using High Speed Impedance, Thesis Texas A & M University, Dec. 2014.

Thorn, Richard, Three-Phase Flow Measurement in the Offshore Oil Industry—Is There a Place for Process Tomography?, 1st World Congress on Industrial Process Tomography, Apr. 1999.

* cited by examiner

METHOD AND SYSTEM FOR CONTINUOUS MONITORING OF THE WATER FRACTION IN AN OIL WELL STREAM

BACKGROUND OF THE INVENTION

Field of the Invention

This invention relates to the field of oil production and recovery. More specifically, this invention relates to a method, system and apparatus for monitoring the water fraction ("watercut") in flowing oil well production fluid, in particular the continuous inline automatic measurement of watercut in highly flooded oil well flows to provide sufficient data to optimize oil recovery and the profitability of each well.

Related Art

A typical oil production well brings to the surface a production fluid which is a complex mixture of liquid hydrocarbons, various gases, water with dissolved minerals and a variety of solids of different sizes. The production fluid from underground reservoirs often includes water or brine, which is referred to as produced water. As the reservoirs of oil mature, especially when secondary or tertiary recovery methods are used, the quantity of produced water increases and often exceeds the volume of the hydrocarbons. The cost of producing, handling, and disposing of the produced water often defines the economic lifetime of an oil field. It is thus important to monitor the amount of produced water—the watercut—in order to optimize the production of oil from a reservoir.

Specifically, watercut is the ratio of the volume of water produced compared to the total volume of liquids produced. While the term watercut has traditionally been used, the API naming is OWD or On-Line Water Determination.

In a typical installation, the flowing production fluid from each well is directed either directly or indirectly through storage tanks, to a separation facility where the hydrocarbons (oil) are separated from the water and the other constituents. It is very difficult, if not impossible, to determine how much water is produced and included in the flowing production fluid coming from each individual well, i.e., the watercut, because the watercut can only be accurately measured after the separation of the water from the production fluid.

The model of flow in an oil well pipeline is a two-phase (liquid and free gas) or a three-component (free gas and a liquid consisting of oil and water) structure. Each component is characterized as a volume fraction of the total flow at the inspection point. The watercut of crude is the ratio of the volume fraction of the water component to the sum of the volume fractions of the water and oil components.

Monitoring the watercut of flowing production fluids is complicated by the fact that as the crude flows from the wellhead to the metering station, the light hydrocarbons in the crude pass from a liquid to a gaseous phase as the pressure in the pipeline decreases along the pipeline length. Additionally, as the crude flows to the metering station and the pressure in the pipeline decreases, the dissolved gas in the crude also passes to a free gaseous phase. Thus, as the flow moves along the pipeline length due to the pressure decrease, the volume fraction of the gas phase increases and, correspondingly, the volume fraction of the liquid phase decreases. This is further complicated in that the longitudinal flow pattern along a length of pipeline is variable and complex. Under the typical conditions of flow along the length of pipeline from the bottom hole to take-up units, the velocity of the oil and water components increases as the pressure decreases along the longitudinal section of the pipeline, and the volume fractions of each component vary along the pipeline length.

Other factors that impact on the accurate determination of watercut in flowing production fluids is that over time the hydrocarbon composition of the oil component is subject to change which results in changes in the electrical physical properties of the oil well flow. This change in the hydrocarbon composition of the oil component can cause measurement errors and be interpreted as a change in the watercut of the crude flow. Additionally, the cross-sectional flow pattern is also variable and complex, due to the configuration of the pipeline, the location of measuring points, flow direction, the value of the settled production rate, pressure, impact of manifold flow, etc.

In summary, the flow of crude from the well to the take-up units is complex and constantly varying both along the length of the pipe and cross-section of pipe making it extremely difficult to accurately measure the watercut of the flowing production fluid and automate production control.

One method used to ascertain the watercut for each individual is through a mobile laboratory that travels from well to well. The technician removes a sample of the production fluid at each individual location and determines in the mobile laboratory the watercut of such sample. Such a method of measuring watercut is unsatisfactory because the characteristics of a flowing crude oil monitored in a pipeline is constantly varying, the method is time consuming and does not determine the "real time" conditions in order to manage production and reservoirs efficiently. (See, INTERSTATE STANDARD GOST 8.589-2007, *State System for Ensuring the Uniformity of Measurements. Conducting Registration Operations on Items of Reception-Delivery of Oil in the Petrowire Systems*).

Watercut meters have been used in the petroleum industry. Several common technologies are dielectric measurements using radio or microwave frequency, NIR (near infrared spectroscopy) measurements and less common are gamma ray based instruments.

More specifically, such automated monitoring of the watercut and compositional analysis of well products of oil fields include measuring the values of the dielectric permeability and the specific electrical conductivity of the well products, and also measuring the flow rate, pressure and temperature of the flowing production fluid. Based on the results of such measurements, the value and amount of the oil, gas and water components of a well product are forecast using programmable equipment, e.g., computers, according to a selected mathematical model. These type systems have not proved to be accurate enough on which to base economic and business decisions. The dielectric permeability and specific electrical conductivity of a medium are determined by its molecular and ion composition and is its unique fingerprint. Any change in the composition, specifically any change in the aggregative state or temperature results in changes in the above electrical physical properties, e.g., dielectric permeability and specific electrical conductivity.

Dielectric permeability of a medium is defined as the ratio of the value of capacitance of a capacitor with a monitored medium between the capacitor plates to the value of electrical capacity of the same capacitor with vacuum or air between the plates.

Specific electrical conductivity is defined as the value of the reciprocal of the electrical resistance of the monitored volume of medium corrected to the electrical resistance of a 10×10×10 mm cube of such medium.

There is however a dependence of these measured values on the frequency of the voltage applied to the medium. This is particularly true in measuring aqueous media. Frequency dependencies arise due to the influence of the near-electrode thin layers at the interface between the solid (electrode) and liquid phase (monitored medium), i.e., there is virtually no dependence on the medium's properties. Thus, such properties of the measuring system do not allow for the exact determination of both dielectric permeability and specific electrical conductivity of just the medium by measurements at a single fixed frequency.

In attempts to accurately determine the electrical physical properties of the crude, a series of measurements of electrical capacity and resistance at a number of frequencies are required that would enable subtracting the influence of the near-electrode layers. Such a series of measurements takes considerable time. Complicating these measurements is the fact that it is difficult to ensure the constancy and invariability of the flowing production fluid during such measurements, particularly under the conditions of flow rates of 1 m/s or more. These circumstances also limit the feasibility and accuracy of attempting to monitor the watercut of the flow by measuring the dielectric permeability and specific electrical conductivity of the medium.

Additionally, it is close to impossible to accurately determine the total fraction of water, oil and gas because of the differences in the dielectric permeability and electrical conductivity of these constituents in flowing production fluid. The dielectric permeability of water is about 40 times higher than the dielectric permeability of oil and 80 times higher than the dielectric permeability of gas. The ratio of the specific electrical conductivity of brine and the specific electrical conductivity of oil and/or gas is even higher.

Thus, there are various factors that impact on the accurate determination of the watercut in flowing crude oil production fluid, including but not limited to, changes in compositional analysis of the flow along the pipeline length due to the pressure decrease; changes in the density of formation water with time, and, as a result, electrical physical properties of the water component; dependence of the specific electrical conductivity and dielectric permeability of the water component on the total dissolved salts; changes in the composition of the oil component with time, and, as a result, electrical physical properties of the oil component; the presence of dissolved gas; the presence of light hydrocarbons.

The method, system and apparatus of this invention minimizes the effect of such variables and enhances accuracy of the determination of watercut in crude oil production fluid flowing in a pipeline.

Examples of prior art systems used for the automated control of water and component compositions of well products from oil deposits are described in Russian Federation Patent Nos. 2329471C1, 2334951C1 and 2336500C1 all to Furmakov et al (OAO Tekhpribor).

These Furmakov patents describe the automated monitoring of the watercut and compositional analysis of well products of oil fields using instruments that measure and monitor the dielectric permeability (electrical capacity) and specific electrical conductivity (electric resistance) of the watercut along with using temperature sensors, pressure transmitters, and flow meters, as well as a programmable device and/or computer workstation. These Furmakov patents have not been widely used in the monitoring of well flows because of the poor accuracy of such watercut measurements compared to analyses made by the laboratory services of oil producers.

Applicant is also aware of the following other references that may be relevant to this invention:

U.S. Pat. No. 5,793,216A to Constant describes a device and method for determining the proportion of a multiphase fluid in a petroleum effluent by irradiating with an electromagnetic field.

RU129256U1 entitled Device for Determining Component Composition Products of Oil-Gas Well (translated) describes measuring in real time the fractional composition flow of a multi component phase that includes oil, gas and water, and also for determining mass and volumetric flow rate. The device includes a section of a pipe wherein there are temperature and pressure sensors, and a system for measuring the electro physical characteristics of the liquid. The outputs of the sensors for measuring the electro physical characteristics are connected to a computing device. The system of measuring electro physical characteristics measures the dielectric permeability and/or electric conductivity, and the device additionally includes an ultrasonic meter, the outputs of which are connected to the computing device. Each of the ultrasonic meters is intended for recording the speed of propagation of and signal amplitude at fixed frequency of acoustic oscillations.

RU2397479C1 to Moskalev Igor' Nikolaevich entitled Device for Measuring Volume for Measuring Volume Ratio of Liquid Phase in Stream of Liquid Natural Gas Mixture (translated) discloses the measuring volume ratio of the liquid phase in a stream of a liquid-gas mixture (LGM) without disturbing the stream. The device has a frequency control unit, a microwave generator, a power divider, a measurement microwave resonator, a reference microwave resonator, an amplitude detector for the measurement resonator, an amplitude detector for the reference resonator, a frequency measurement and processing unit, a pressure sensor and a temperature sensor.

RU59239U1 entitled Complex Component Wise Flow discloses the use of radio wave high frequency probing in two mutually-orthogonal directions to measure relative content of the components of oil well flow.

RU 2063615 entitled Method of Measurement of Component-by Component Flow of Three Component Gas and Liquid Flow and device for its Implementation for measuring in real time the fractional composition (percentage phase relation) flow of a three component-phase medium, including oil, gas and water.

Other references are:

RU2484381C1 entitled Continuous Monitoring Method and System of Availability and Localization of Section of Interpenetration of Network Heat Carrier and Heated Water in Heat Exchange Equipment of Centralized Heat Supply System.

RU2522316C1 entitled Automated Process Control Method and System in Primary Settling Tanks, Secondary Settling Tanks and/or Sludge Consolidation Tanks at Waste Water Treatment Plants of Housing and Utilities Infrastructure.

RU2498286C1 entitled Method and System for Controlling Commercial Gasoline Blending.

RU2488109C2 entitled Method for Recognition and Identification of Batches of Strong Liquors, Mainly-Vodka.

RU2479036C1 entitled Method to Recognize and Identify Batches of Commercial Petrols.

RU104727U1 entitled Primary Converter for Measuring the Electrical Capacitance (Dielectric Constant) I of the Electrical Resistance (Specific Conductivity) of Liquid or Gas RU2571788C1 entitled Method and System for Automated Control over Oil Well Stream Watering.

KR 10-0489813 to Kim, Myung Sool
CN 2043741340 to Yao Yuping
CN 201689071U to Fang Zaixin.
CN 104820000A to Wu Yanfeng
CN 101865873B to Fang Zaixin.
US 2015/0083402 to Manin.
US 2013/0110411 to Black et al.
US 2012/0017697 to Benzo et al.
US 2008/0288181 to Lucero.
US 2006/0247869 to Lucero.
US 2004/0253735 to Vadgama et al.
U.S. Pat. No. 8,505,363 to Masek.
U.S. Pat. No. 7,293,471 to Lund Bo et al.
U.S. Pat. No. 7,201,068 to Foss et al.
U.S. Pat. No. 6,945,122 to Foss et al.
U.S. Pat. No. 6,318,156 to Dutton et al.
U.S. Pat. No. 6,292,756 to Lievois et al.
U.S. Pat. No. 6,272,915 to Kostelnicek et al.
U.S. Pat. No. 6,076,049 to Lievois (Abstract)
U.S. Pat. No. 6,097,786 to Groves et al.
U.S. Pat. No. 5,793,216 to Constant Burak, Erdogan, *Watercut Measurement Method Using High Speed Impedance*, Texas A & M University, December 2014.

Rodriguez, Iara H., et al. *Capacitive wire-mesh sensor Measurements in oil-water flow*, Petroleum Engineering Dept. Unicamp, Campinas, SD, Brazil (p 2190).

Hammer, Erling A., *Capacitance transducers-Basic Principles*

Zubair, Muhammad, *A High Resolution Capacitive Sensing System for the Measurement of Water Content in Crude Oil; Sensors* 2014, 14, 11351-11361. Published Jun. 25, 2014.

SUMMARY OF THE INVENTION

The present invention provides a method, system and apparatus for continuously determining and monitoring watercut in a flowing production fluid of oil, water and gas (and other constituents) flowing through a pipeline from an oil reservoir. The method comprises providing an impedance sensor unit, e.g., an electrochemical impedance sensor unit, at a fixed location in the pipeline of the flowing production fluid in the pipeline for continuously measuring the impedance value of the flowing production fluid at such location in the pipeline. Initially, a sample and optionally several samples of the production fluid are obtained from the pipeline, ideally close to or proximate the fixed location in the pipeline, to determine a watercut value of the sample(s). From such watercut value from the sample, a correlation formula is determined of the watercut value of the sample with the measured impedance values at the fixed location. Subsequently, the continuously measured impedance values are inputted into the correlation formula to continuously calculate the watercut value of the flowing production fluid at the fixed location.

In a preferred method an impedance sensor unit and a temperature sensor are provided at a fixed location in the pipeline. The sensor unit continuously measures the impedance values and temperature of the flowing production fluid in the pipeline at the fixed location in the pipeline. At least one sample, and optionally more than one sample, of the production fluid during a shutdown of the fluid flow is removed from the pipeline close to or proximate the fixed location in the pipeline to determine the watercut value of the sample. A correlation formula is then determined of the watercut value (s) of the sample(s) with the measured impedance values and temperatures at the fixed location. A computer is then programmed with the correlation formula to provide a programmed computer to calculate the watercut from impedance values inputted into the computer. Subsequently, the continuously measured impedance values and temperature of the flowing production fluid are inputted into the programmed computer to continuously calculate the watercut value of the flowing production fluid at the fixed location.

This invention is also directed to a sensor unit for continuously determining and monitoring the watercut in a production fluid flowing through a pipeline from an oil reservoir. The sensor unit comprises an impedance sensor unit for measuring impedance values of the flowing production fluid, a temperature sensor unit for measuring a temperature values in the flowing production fluid, a means for mounting the sensory unit in the pipeline wherein the impedance sensor unit and temperature sensor unit continuously measure the impedance values and temperature values of the flowing production fluid. A means is provided for communicating the continuously measured impedance values and temperature values to a programmed computer for calculating the continuous watercut values of the flowing production fluid and displaying such watercut values on a display monitor, e.g., computer monitor. Preferably, the impedance sensor and temperature sensor are combined into one unitary sensor unit.

Other sensors can be added to measure pressure and density of the flowing production fluid and the total rate of flow of oil. Data collected and generated can be communicated to a data collection device (computer) for monitoring.

BRIEF DESCRIPTION OF THE DRAWINGS

The preferred and alternative embodiments of the present invention are described in detail below with reference to the following drawings.

DETAILED DESCRIPTION OF THE INVENTION

This invention is directed to the continuous automated monitoring of the watercut of flowing production fluid from oil fields with an apparatus for measuring the impedance value characteristics and temperature of the flowing production fluid at the inspection point in combination with a programmable device and/or workstation for monitoring the measurements.

The present invention provides both a method, system and an apparatus for the upstream oil industry engineers to ascertain accurately the real time, inline watercut information from each well. This invention minimizes the disadvantages of the prior art and enhances the accuracy of determining the watercut in crude oil flowing in a pipeline on a continuous and automated basis. The data obtained from such automated and continuous monitoring of the watercut supports the managerial decisions made by oil production enterprises to optimize the production and distribution of the oil products from the oil field wells.

This invention is directed to an accurate inline determination of water content in unaltered or un-separated well flow in the presence of oil, gas and other foreign matter such as sand using based on the determination of electro-chemical impedance Z of the well flow (flowing production fluid).

This invention is further directed to the quantitative determination of electro-chemical impedance for complex well flow, such as flow containing unknown and changing quantities of oil, water, including water with salt, gas and other solid components such as sand and particles of dirt and rock. The invention uses the concept of measurement of electrical properties of the well flow (flowing production fluid) and comparing the electrical measurements against pre-determined mathematical models of the complex flow (conversion formulas) with the purpose of determining the best possible mathematical model applicable to the well flow with the purpose of using such mathematical model for the purposes of calculation of water content (watercut) in the well flow.

The method, system and apparatus of this invention is used for the inline quantitative determination of water content in unaltered or un-separated well flow in simultaneous presence of oil, gas and other foreign matter such as sand using method of experimental determination of electrochemical impedance of said well flow installed into any section (vertical or horizontal) of a pipeline running from well head to a primary or secondary oil processing facility or in a pipeline anywhere in the oil processing facility with the purpose of knowing specific and accurate fraction of water contained in the well flow.

The sensor unit for such inline quantitative determination of water content in such flowing production fluid is comprised of two or more electrodes inserted into the pipeline through which passes the unaltered well flow or production fluid, the water content of which needs to be determined. Some of the electrodes (induction electrodes) are connected to a source of alternating current with the current frequencies having a broad range. The alternating current in turn induces alternating voltage and current on some of these electrodes (measurement electrodes). The apparatus then measures these induced values for voltage and current at a number of frequencies to determine the impedance value for each frequency.

This invention utilizes as a feature the measurement of the impedance value of the production fluid flowing through an oil well pipeline. Electro chemical impedance value Z is a complex resistance of an electro-chemical system produced by an alternating current passing through such system. Such impedance value Z can be determined as total resistance of a system and is represented mathematically as a complex number:

$$Z = Z' + jZ'' = Re + jIm,$$

Z' or Re=real component, and Z" or Im=imaginary components of the total impedance value Z of a system and j represents unit imaginary number.

The total resistance (impedance Z) of a system is a relationship between current and voltage in such a system which allows us to use electrical elements and equivalent circuits for the purposes of modeling such impedance value.

The total impedance Z is $Z = R - j/\omega C$ where resistor impedance Z' is equal to R, capacitance impedance Z" is equal to $-j/\omega C$.

In this invention the numerical evaluation of Z as a function of frequency of alternating current is used for the determination of the watercut of the flowing production fluid.

Figure 1:
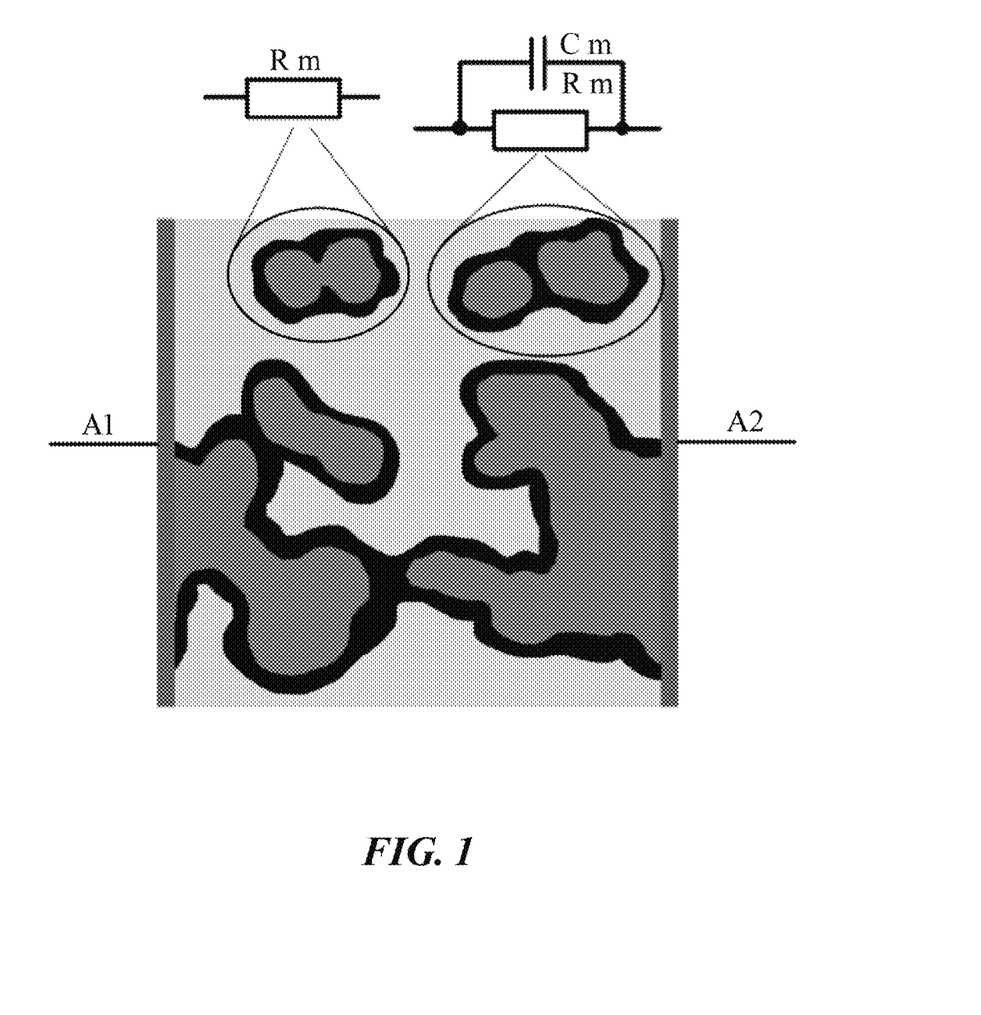
FIG. 1 is schematic representation of a number of physical models of water (gray) encapsulated by oil (black) flowing in a pipeline and models of the electrical equivalent circuits of such physical models.

FIG. 1 is schematic representation of a number of physical models of water (gray) encapsulated by oil (black) flowing in a pipeline and models of the electrical equivalent circuits of such physical models. The simplest equivalent circuits are shown in this Figure. At the simplest level, a droplet of water (conductor) coated with a layer of oil (dielectric) can be approximated electrically via resistor Rm and two separate droplets of water embedded in a larger globule of oil can be approximated electrically via Rm and Cm connected in parallel. Thus in its simplest representation, the electro chemical properties of a mixture of oil and water can be represented by an electrical circuit consisting of a collection of electrical resistors R and electrical capacitors C, such as shown in FIG. 1.

Given the highly complex nature of flowing production fluid, one may require one or more equivalent circuits at any moment in time in order to explain the electrical parameters of the medium passing between the electrodes measuring impedance value. A pre-determined mathematical model of each theoretically possible equivalent circuit and combinations thereof, combined with high speed computing, allows for the real time determination of the best possible equivalent circuit combination fit to the experimentally determined electrical parameters and consequently, for the optimum accurate determination of the watercut.

Figure 2:
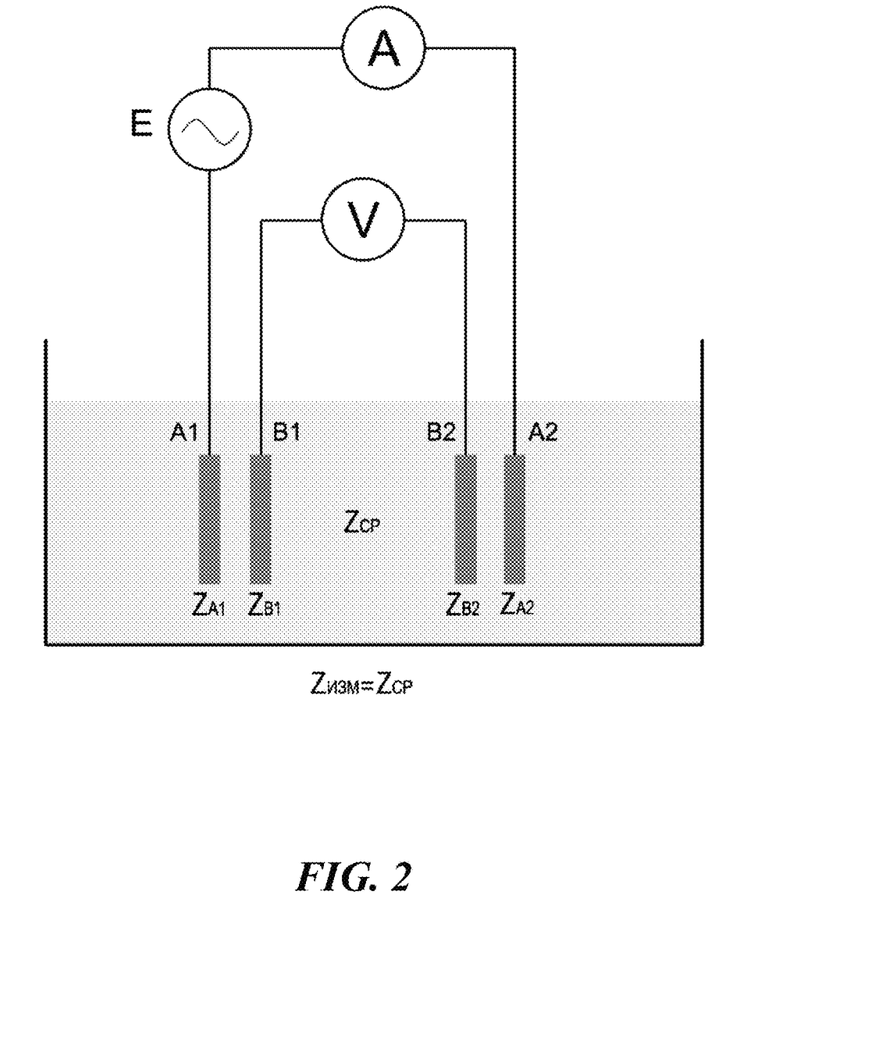
FIG. 2 is a schematic view of a four electrode electro chemical cell where electrodes B1 and B2 measure the induced potential in the volume of fluid, E is a source of alternating current, A is an ammeter, V is a voltmeter, and electrodes A1 and A2 induce an alternating voltage and current in the volume of fluid.
Figure 8:
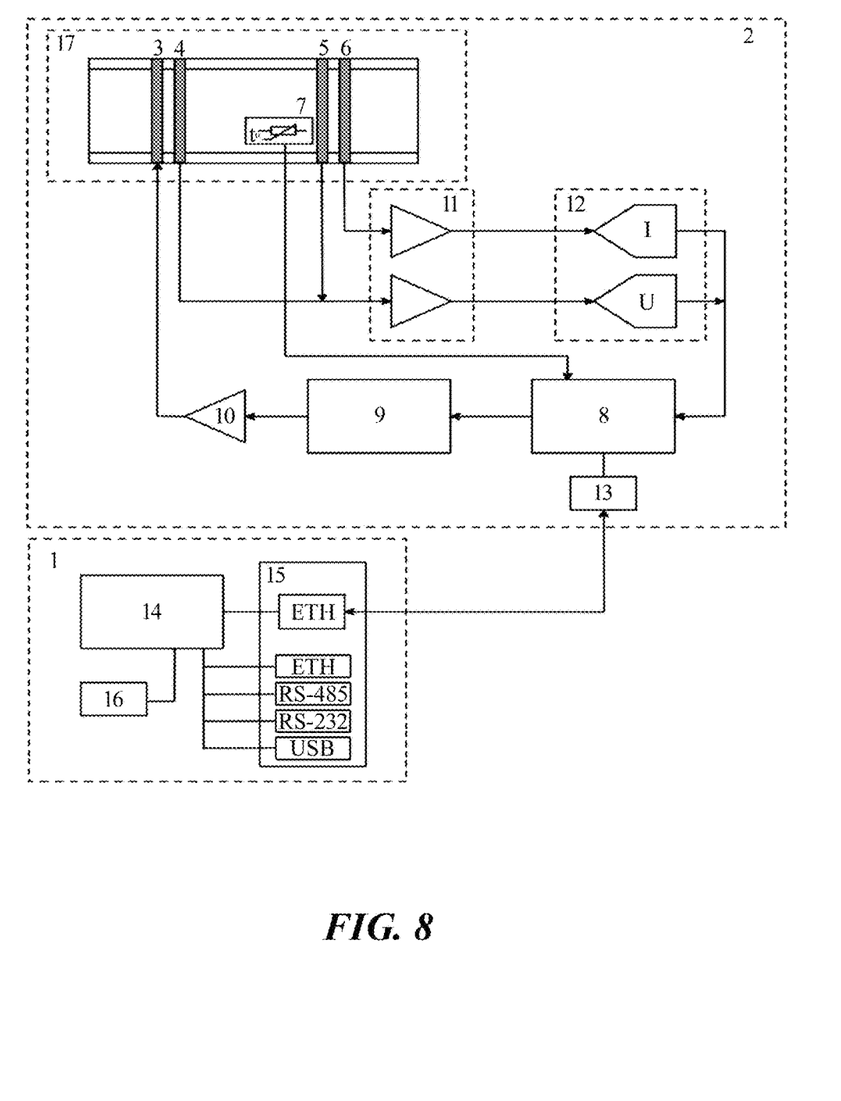
FIG. 8 is a block diagram of an impedance sensor unit used in the method and system for the continuous monitoring of the watercut or water fraction in a flowing oil well stream.

FIG. 2 herein is a schematic view of a four electrode electro chemical cell where electrodes B1 and B2 measure the induced potential in the volume of fluid, E is a source of alternating current, A is an ammeter, V is a voltmeter, and electrodes A1 and A2 induce an alternating voltage and current in the volume of fluid. This schematic representation of a four electrode electro chemical cell is used to explain the function of the impedance sensor unit of this invention used to measure impedance value of the production stream and which is correlated with the watercut of the stream. FIG. 8 is a more detailed schematic of such sensor unit.

Referring to FIG. 2, E is a source of alternating current, A is an ammeter, V is a voltmeter, electrodes A1 and A2 induce alternating voltage and current in fluid volume and electrodes B1 and B2 measure induced potential in the measured volume. In the impedance sensor unit used to measure the impedance value in the production fluid, an alternating current of varying frequency (ranging from 0.1 Hz to 10.0 MHz) and varying amplitude is applied to electrodes A1 and A2. Electrodes B1 and B2 are used to measure the potential in the fluid induced by electrodes A1 and A2. The momentary values of alternating current in the fluid are measured on electrodes A1 and A2.

To achieve a high accuracy in the measurement of potential between B1 and B2, the apparatus is designed in such a way as to reduce heat dissipation in the measurement tract and reduce polarization effects on B1 and B2 (or 4 and 5 in the FIG. 8).

Figure 3:
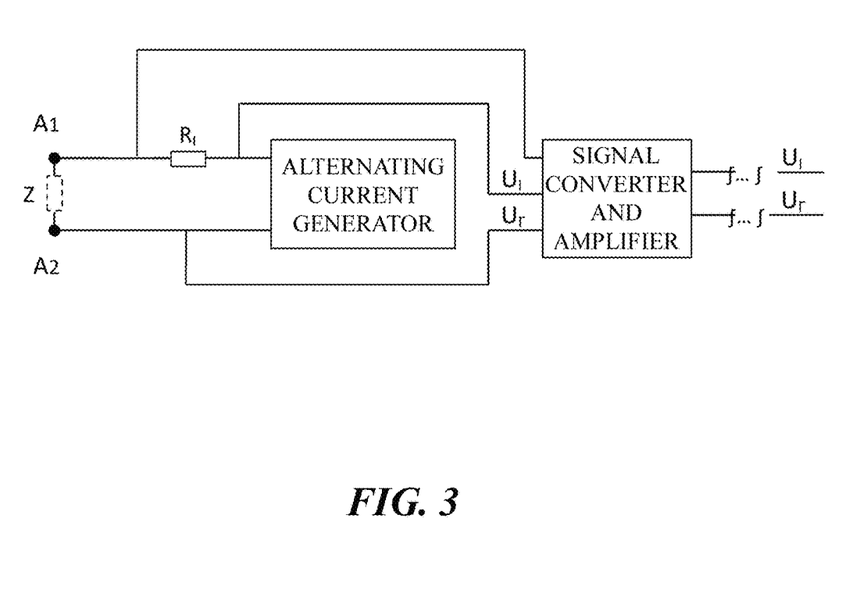
FIG. 3 is a schematic of a measurement block of an impedance sensor unit (a transducer unit) for determining the watercut in a pipeline of flowing crude by measuring impedance value where A1, A2 are electrodes and Z is the electrochemical impedance value.

FIG. 3 is a schematic of a measurement block of an impedance sensor unit for determining the watercut in a pipeline of flowing crude by measuring impedance value where A1, A2 are, for example, two electrodes and Z is the electrochemical impedance value. With the application of an alternating current at a fixed frequency to an electro-chemical cell, impedance Z is measured using electrodes A1 and A2 and will simultaneously register two sine curves of the same frequency. One of the sine curves will correspond to alternating voltage across Ur across the cell and other one corresponding to the alternating current Ui across the cell.

Figure 4:
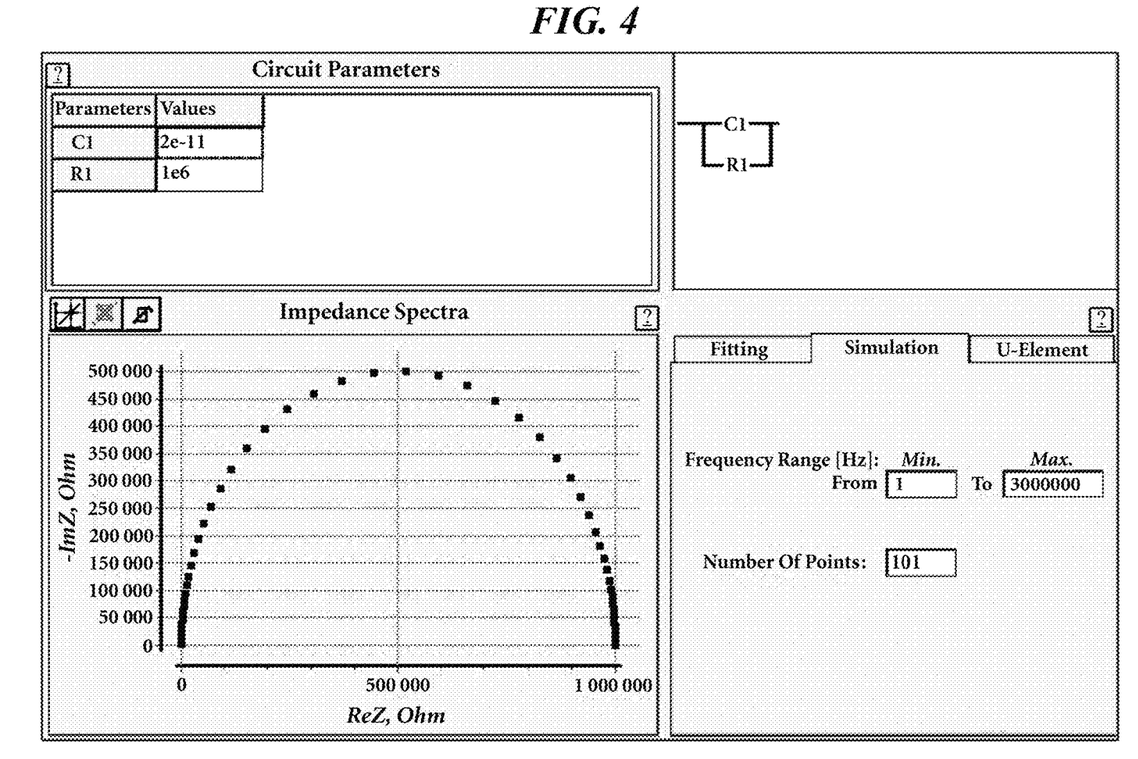
FIG. 4 is a Nyquist Plot created by measuring the electrochemical impedance value Z at a number of frequencies to determine an equivalent circuit C (upper right corner of FIG. 4).
Figure 5:
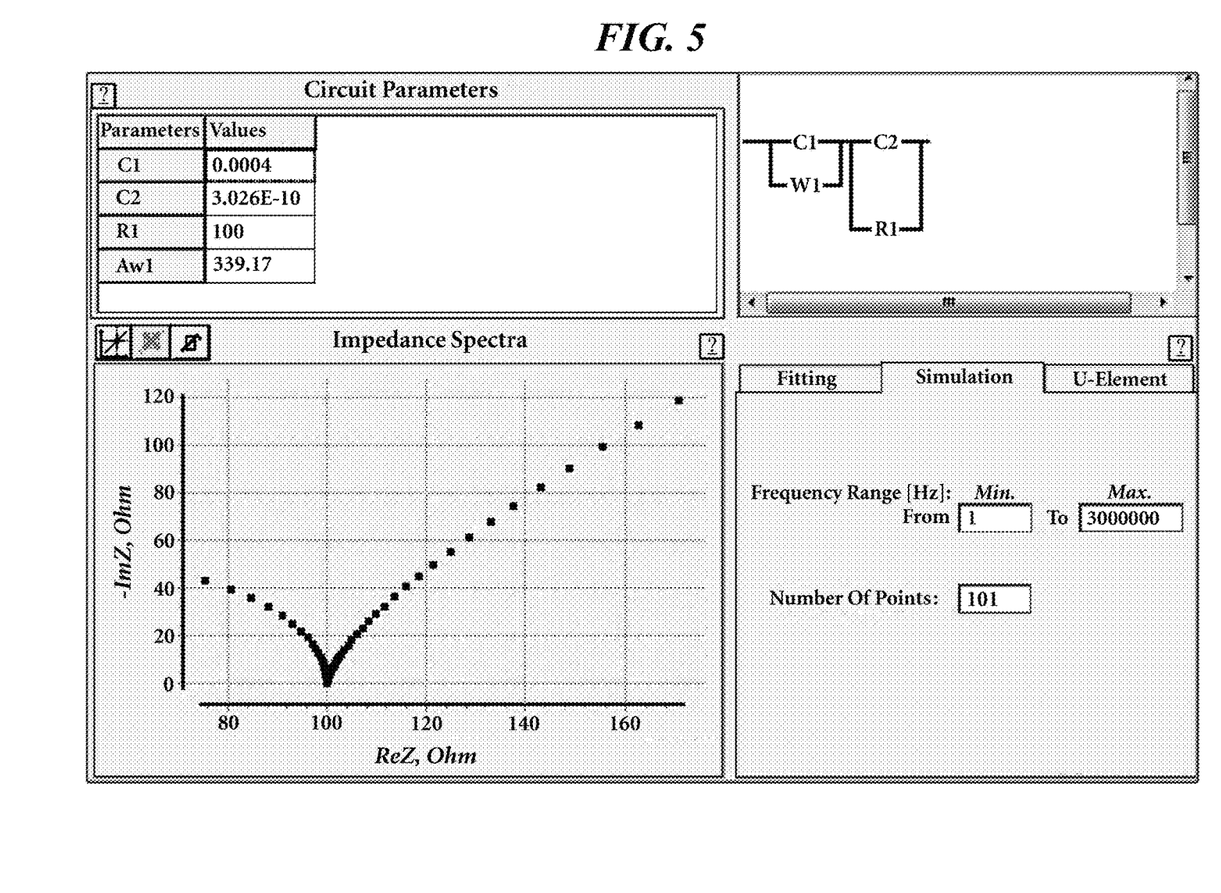
FIG. 5 is another Nyquist Plot created by measuring the electrochemical impedance value Z at a number of frequencies to determine another equivalent circuit C (upper right corner of FIG. 5).
Figure 6:
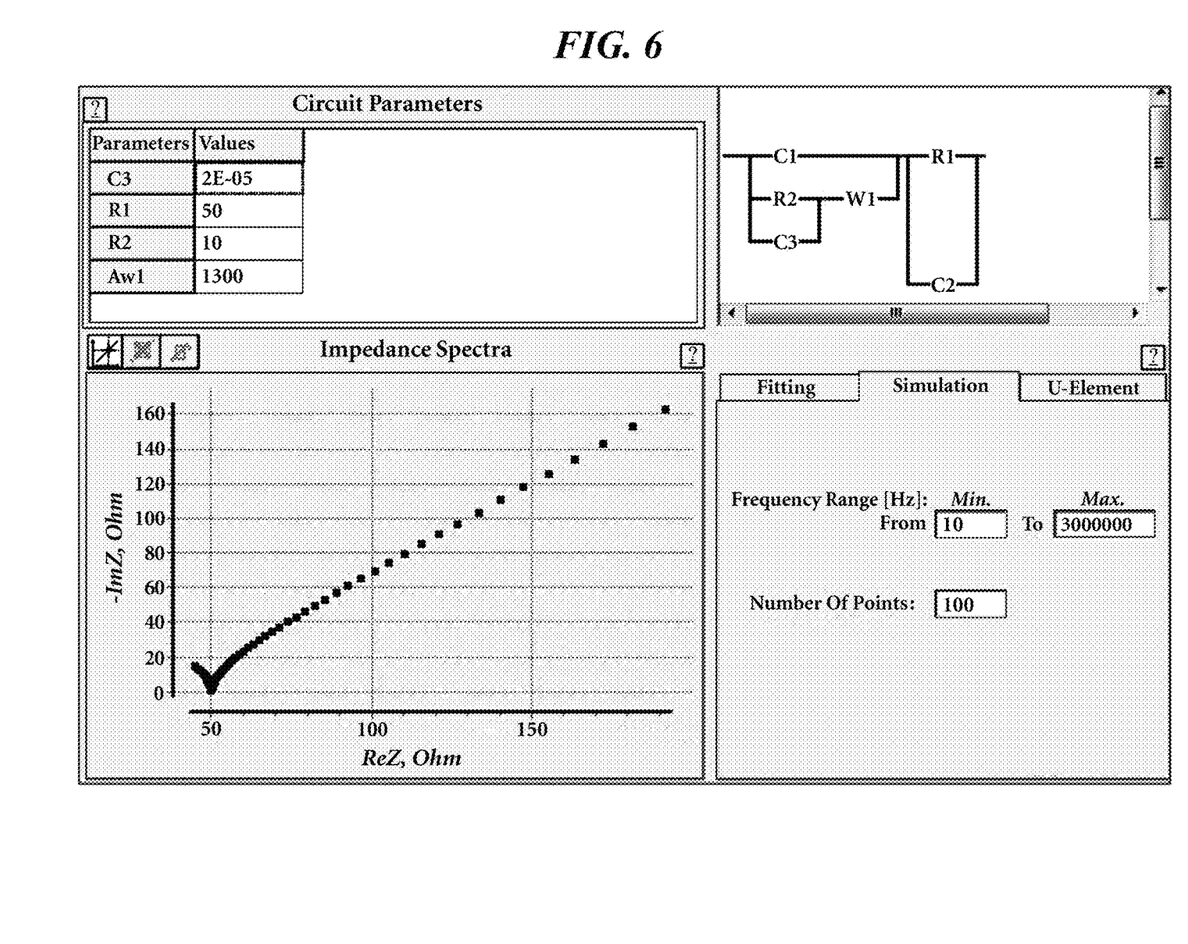
FIG. 6 is another Nyquist Plot created by measuring the electrochemical impedance value Z at a number of frequencies to determine another equivalent circuit C (upper right corner of FIG. 6).

Referring to FIG. 4 is a Nyquist Plot created by measuring the electrochemical impedance Z at a number of frequencies to determine an equivalent circuit C (upper right corner of FIG. 4). The measurement of the amplitude and phase characteristics of these two sine waves gives us the data necessary to calculate absolute value of electro-chemical impedance Z at a single frequency as well as the phase shift between real and imaginary components Z' and Z" respectively. We then repeat this process at a number of frequencies and use this Z (ω) data to plot complex Z in Z', Z" coordinates (so called Nyquist plot, as shown on FIG. 4 and the equivalent circuit. FIGS. 5 and 6 are additional examples of the Nyquist plot and corresponding equivalent circuits.

Figure 7:
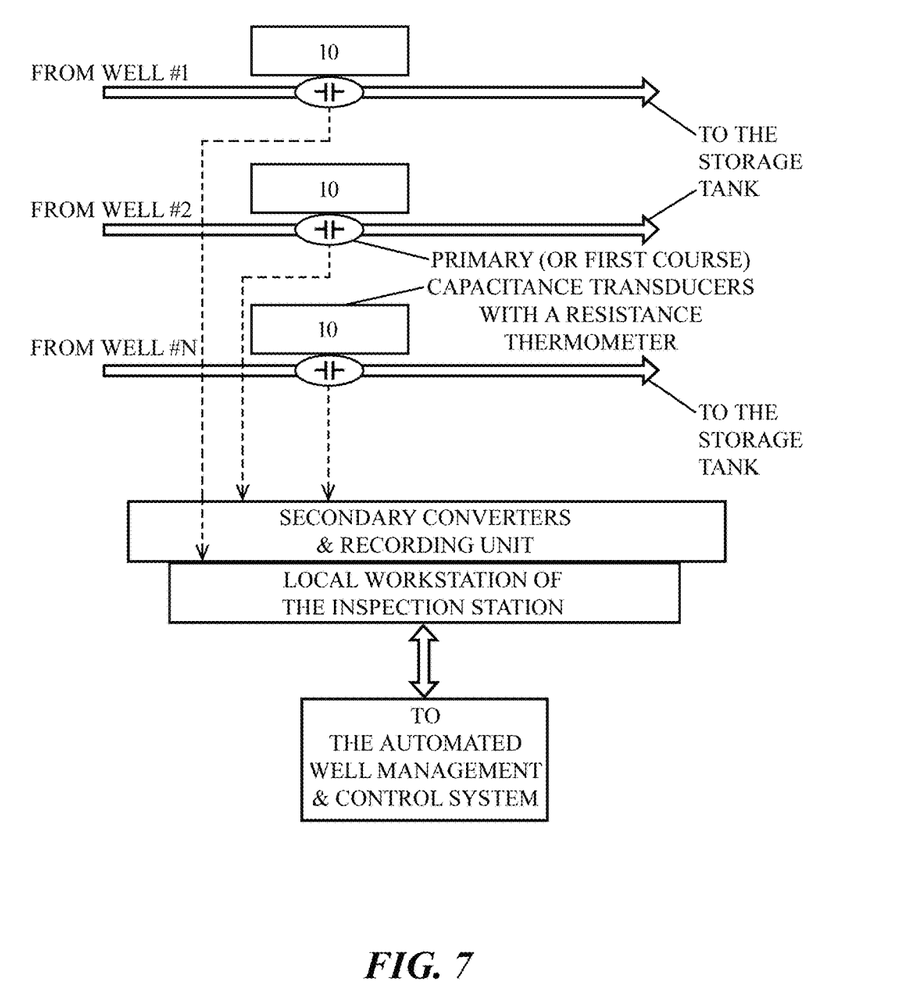
FIG. 7 is a flow chart showing a system for the use of data from multiple impedance sensor units mounted in a plurality of pipelines from several wells, e.g., #1, #2, and #N, to storage tanks, wherein the sensor data is transmitted to a control system and the data is used to determine the watercut of the flowing production fluid and assist in automating well management.

FIG. 7 is a flow chart showing a system for the use of data from multiple impedance sensor units 10, i.e., transducer units, mounted in a plurality of pipelines from several wells, e.g., #1, #2, and #N, to storage tanks, wherein the sensor data is transmitted to a control system and the data is used to determine the watercut and assist in automating well management. The proposed method for the automated and continuous monitoring of the watercut of oil products from a well, i.e., wells 1, 2 . . . N includes measuring the impedance values, and preferably also the temperature of the flowing production fluid, at a point in each pipeline with the impedance sensor units 10. The impedance values are transmitted to a programmable computer that converts the impedance values to watercut value. This is accomplished through a predetermined mathematical model—correlation formula—that is programmed into the computer to determine the watercut in the pipeline from such measured impedance values.

The complex impedance value of the well product and its components are measured continuously at a fixed frequency of electric field exposure, with the measured values of the complex impedance value and its components corrected to the normal (standard) conditions, e.g., 20° C. and the above determination of watercut calculated.

Still referring to FIG. 7, in the proposed operation of the automated monitoring system, an impedance sensor unit 10 has electrodes inserted into the pipeline through which the fluid flows. The sensor unit 10 is generally located along the flow path at the bottom of the cross section of a horizontal pipeline near the wellhead. The vertical dimensions of the impedance sensor unit 10 electrodes should not exceed the height of the liquid phase flowing through the pipe. Such a location ensures the natural flow separation. The horizontal dimension and electrode gaps of the impedance sensor unit 10 are determined by optimizing the measured variables of the complex impedance value of the medium. Generally, these dimensions are about 10-30 mm (horizontal dimension) and about 5-12 mm (electrode gap) respectively.

FIG. 8 is a block diagram of an impedance sensor unit used in the method and system for the continuous monitoring of the watercut value or water fraction in an oil well stream.

More specifically:

Elements 3 and 6 are current electrodes;

Elements 4 and 5 are electrodes used to measure potential induced by electrodes 3 and 6;

Element 7 is a temperature measurement block;

The apparatus electronic blocks are comprised of frequency generator 9; amplifiers 10 and 11; analog to digital converters 12; CPU 8; Ethernet interface module 13; 2 is the impedance sensor unit; 14 is computer which has mathematical algorithms programmed in to convert the impedance values to watercut values; 15 interface module; and 16 is wireless communication module.

In general, the impedance sensor unit 17 includes a transducer located within the flow space of the flowing production fluid while the oil is flowing through the pipeline. High capacity signal processor 8 converts the momentary current and potential (voltage) values measured by electrode block 17 into complex values of current $\dot{I}$ and $\tilde{U}$ using a Fourier transform. The complex medium impedance $\dot{Z}$ is calculated dividing complex voltage $\tilde{U}$ by complex current $\dot{I}$.

Figure 9:
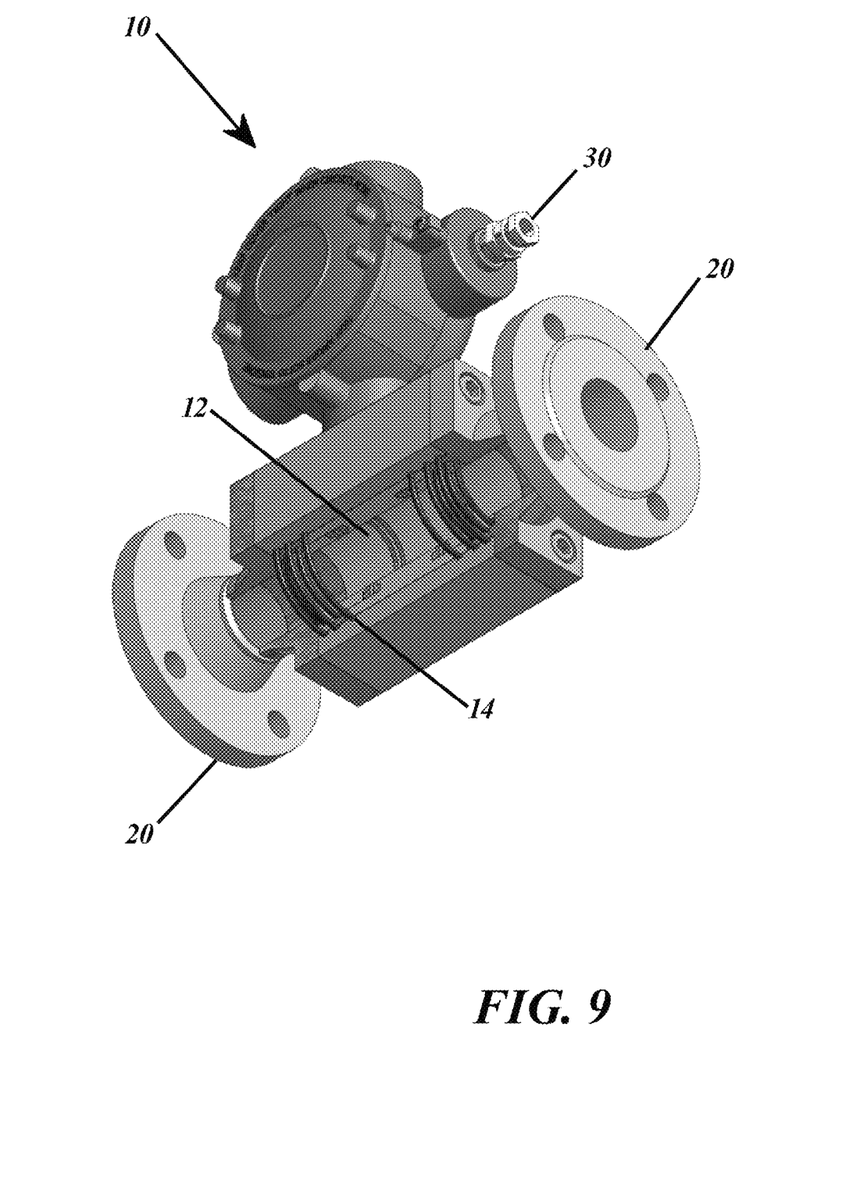
FIG. 9 is a perspective view of an embodiment of an impedance sensor unit 10 for measuring the impedance value of the flowing oil production fluid for determining watercut, with a portion of the impedance sensor unit cut-away for viewing the interior of the unit. The unit 10 is ready to be installed directly into the well flow pipeline using, for example, a flanged connection 20, with a signal processing unit (a computer, not shown) attached to the impedance sensor unit by means of a cable (not shown) connected to the impedance sensor unit at cable port 30.

FIG. 9 is a perspective view of an embodiment of an impedance sensor unit 10 for measuring the impedance value of the flowing oil production fluid for determining watercut, with a portion of the impedance sensor unit cut-away for viewing the interior of the unit. The unit 10 is ready to be installed directly into the well flow pipeline using, for example, a flanged connection 20, with a signal processing unit (a computer, not shown) attached to the impedance sensor unit by means of a cable (not shown) connected to the impedance sensor unit at cable port 30.

The impedance sensor unit 10 consists of a tubular body 12 with an internal diameter substantially the same as the internal diameter of the pipeline that transports the production fluid. The impedance sensor unit 10 is fitted into the pipeline at a fixed location with the flanged connections 20 on each side of the impedance sensor unit 10. The flanged connections 20 can be of any type which permits a secure installation of the impedance sensor unit 10 into a section of the pipeline carrying the production fluid from the oil production well. The tubular body 12 of the impedance sensor unit 10 contains a plurality of electrodes 14, comprised of a minimum of 2 electrodes 14. The preferred maximum is 6 electrodes 14. The electrodes depicted in FIG. 9 are in the shape of rings following the contour of the interior of the tubular body 12 and substantially flush with the interior surface of the tubular body 12. A signal processing unit (a computer) is connected to the impedance sensor unit by means of a cable or a mechanical attachment (not shown) to connector 30

Figures 10, 11:
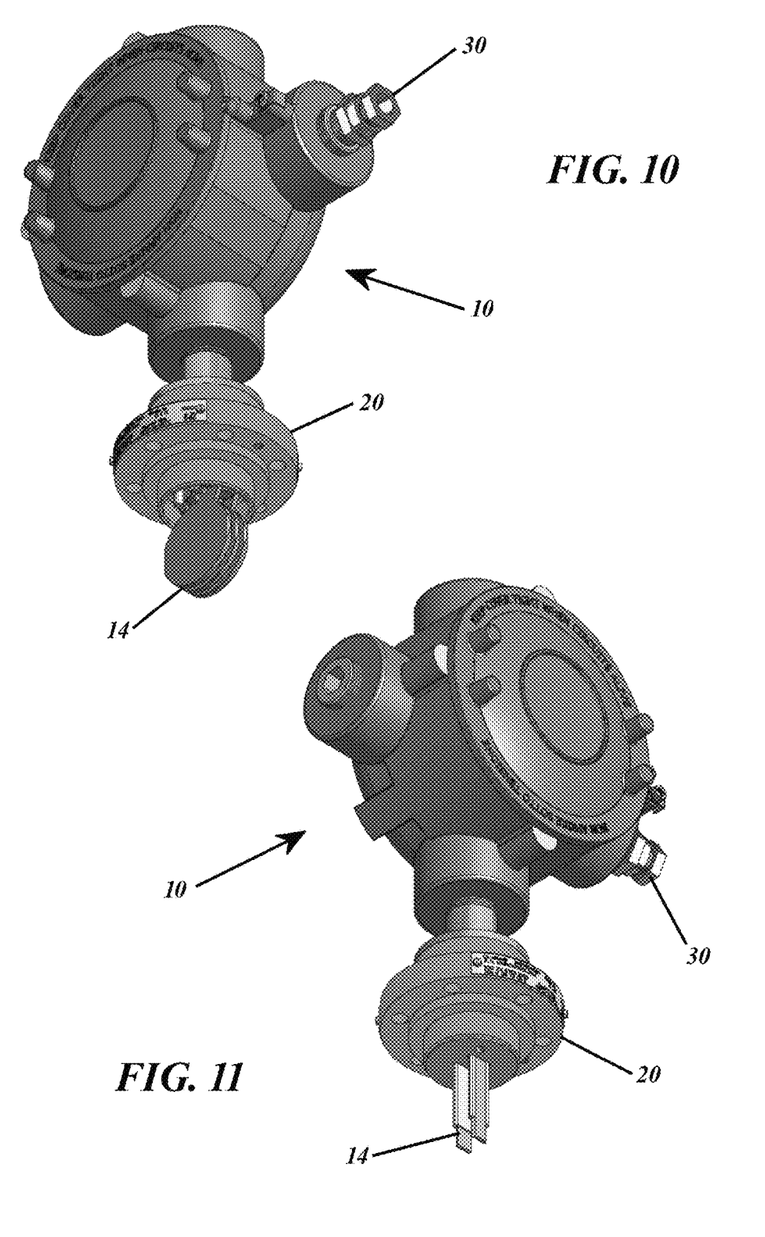
FIGS. 10 and 11 are perspective views of other embodiments of the impedance sensor unit 10 ready to be installed directly into the pipeline for an flowing oil production fluid using a flanged connection 20, with a signal processing unit (a computer, not shown) attached to the sensor unit by means of a cable (not shown) connected to the unit at cable port 30.

Optionally, as shown in FIGS. 10 and 11 the impedance sensor unit can be mounted to the exterior of the production pipeline, mounted in place by flange 20 and have the electrodes 14, for example as parallel circular plates (FIG. 10) or parallel rectangular plates (FIG. 11) (or a combination of thereof) protruding directly into the flowing production fluid pipeline. The impedance sensor units 10 shown, for example, in FIGS. 10 and 11, are installed directly into the well flow using the flange connection 20 (or other type connection) with a signal processing unit (a computer) connected to the impedance sensor unit 10 by means of a cable or a mechanical attachment (not shown) to connector 30.

The electrode system in the impedance sensor unit 10 is made of a corrosion and oxidation resistant conducting material. The entire impedance sensor unit is designed to sustain operating temperatures up to 300° C. and operating pressure of up to 40 MPa. The dimensions of electrodes 14 are determined by the dimensions of the pipeline where the impedance sensor unit 10 is to be fitted. In the sensors of FIGS. 10 and 11 the electrodes are embedded into block of dielectric material, such as polyamide, and are electrically connected to a signal processing unit through port connector 30.

The calibration of the system as described herein of this invention is performed using the following exemplary procedure. Other procedures for calibration may be used. The well to be monitored is shut down for at least a half hour (30 minutes) during which the components of the production fluid segregate into a liquid column. The production fluid is then sampled. The well is then restarted. The sample is then sent to the laboratory for a determination of the watercut value. The watercut value is then calibrated with the continuous impedance sensor unit determinations of impedance values obtained from the flowing production fluid. Occasional laboratory control using samples of the well flow can be performed in order to maintain the monitoring error at the adequate level, the results of the laboratory control are entered in the system and carry out the automatic adjustment of the down-hole constants based on the results of the laboratory control.

Such a calibration procedure is accurate for watercut values within a wide range. Based on the results of the laboratory control and the concurrent results of the automatic monitoring of the impedance values of the flow by the impedance sensor units, an individual correlation formula and its down-hole constants are determined according to a selected mathematical model (dependence) with the system correction to normal conditions.

Such correlation formula may be, e.g., a formula of the following type:

$$W = A \times |Z| + B \times |Z| \times T + C/T + D, \text{ where}$$

W=watercut, %
|Z|=amplitude of complex impedance, ohms;
T=temperature, ° C.;
A, B, C, D=empirical down-hole constants with the appropriate units of measurement.

The watercut of the well flow can thus be monitored continuously by the impedance sensor units of this invention when calibrated as described using the correlation formula.

Based on the sampling procedure, calculated values are obtained for the empirical correlation formula and a correlation formula for each well is generated.

In generating the correlation formula, the temperature is also taken into account. Using the results of the laboratory control minimizes the impact of the quantity of light hydrocarbons, dissolved and free gas, density of formation water and hydrocarbon composition of oil, i.e. individual characteristics of the well.

Thus, the method and system for the automated monitoring of the watercut of oil well flowing production fluids comprises:

The direct continuous measurement of the complex impedance value of the flowing production fluid at a fixed frequency of electric field exposure is carried out with the simultaneous continuous measurement of temperature of the flowing production fluid. These measurements are taken at least once every 1-10 seconds. The complex impedance value and its components are then corrected to the normal temperature conditions (20±5° C.). To this end, the arrays of the recorded instant values of transducer current and voltage, i.e., impedance sensor unit, and measured temperature values for each monitoring channel from the secondary converters unit are communicated or transferred to the programmable device and/or monitoring workstation.

The values of the complex impedance and its active and reactive components are then calculated based on the acquired data arrays for each channel of monitoring the electrical physical parameters.

While various changes may be made in the detailed construction and processes of this invention, it will be understood that such changes will be within the spirit and scope of the present invention. Having thus described the invention in detail, it is to be understood that the foregoing description is not intended to limit the spirit and scope thereof. What is desired to be protected by Letters Patent is set forth in the appended claims.

What is claimed:

1. A method of continuously determining and monitoring watercut in a production fluid flowing through a pipeline from an oil reservoir, the flowing production fluid comprising oil, water and gas, the method comprising:
   a. providing an impedance sensor unit at a fixed location in the pipeline for continuously measuring impedance values of the flowing production fluid in the pipeline, wherein the impedance sensor unit comprising at least one current electrode that is coupled to a first amplifier, at least one voltage electrode that is coupled to the first amplifier, an analog to digital converter (ADC) that is coupled to the first amplifier, a microprocessor; wherein the microprocessor includes a plurality of terminals, a first terminal that is coupled to the ADC and a second terminal that is coupled to a frequency generator; wherein a terminal of the frequency generator is coupled to a second amplifier and the second amplifier is coupled to the at least one current electrodes; wherein the microprocessor is in communication with a computer, via an Ethernet interface module, configured to convert the impedance values to watercut values;

b. continuously measuring the impedance value of the flowing production fluid at the fixed location in the pipeline;

c. obtaining a sample of the production fluid from the pipeline proximate the fixed location in the pipeline to determine a watercut value of the sample;

d. determining a correlation formula of the watercut value of the sample with the measured impedance value at the fixed location at the time of obtaining the sample;

e. Subsequently inputting the continuously measured impedance values into the correlation formula to continuously calculate the watercut value of the flowing production fluid at the fixed location to thereby continuously determine the watercut of the flowing production fluid at the fixed location.

2. The method of claim 1, further comprising repeating steps c., d., and e.

3. The method of claim 1, further including continuously measuring the temperature of the flowing production fluid at the fixed location and determining the correlation formula of the watercut value of the samples with the measured impedance value and temperature.

4. The method of claim 1, wherein obtaining the sample of the flowing production fluid from the pipeline consists of removing the sample of the production fluid during a shutdown of the fluid flow through the pipeline.

5. The method of claim 1, wherein the correlation formula is:

$$W=A\times|Z|+B\times|Z|\times T+C/T+D, \text{ where}$$

W=watercut,
|Z|=amplitude of complex impedance, ohms;
T=temperature, ° C.;
A, B, C, D=empirically determined constants.

6. A method of continuously determining and monitoring watercut in a production fluid flowing through a pipeline from an oil reservoir, the flowing production fluid comprising oil and water, the method comprising:

a. providing an impedance sensor unit and a temperature sensor at a fixed location in the pipeline for continuously measuring impedance values and temperature of the flowing production fluid in the pipeline, wherein the impedance sensor unit comprising at least one current electrode that is coupled to a first amplifier, at least one voltage electrode that is coupled to the first amplifier, an analog to digital converter (ADC) that is coupled to the first amplifier, a microprocessor; wherein the microprocessor includes a plurality of terminals, a first terminal that is coupled to the ADC and a second terminal that is coupled to a frequency generator; wherein a terminal of the frequency generator is coupled to a second amplifier and the second amplifier is coupled to the at least one current electrodes; wherein the microprocessor is in communication with a computer, via an Ethernet interface module, configured to convert the impedance values to watercut values;

b. continuously measuring the impedance value and temperature of the flowing production fluid at the fixed location in the pipeline;

c. removing a sample of the production fluid during a shutdown of the fluid flow through the pipeline proximate the fixed location in the pipeline to determine a watercut value of the sample;

d. determining a correlation formula of the watercut value of the sample with the measured impedance value and temperature at the fixed location at the time of obtaining the sample;

e. Subsequently inputting the continuously measured impedance values and temperature of the flowing production fluid into the correlation formula to continuously calculate the watercut value of the flowing production fluid at the fixed location to thereby continuously determine the watercut of the flowing production fluid at the fixed location.

7. The method of claim 6, further comprising repeating steps c., d., and e.

8. The method of claim 6, wherein the correlation formula is:

$$W=A\times|Z|+B\times|Z|\times T+C/T+D, \text{ where}$$

W=watercut,
|Z|=amplitude of complex impedance, ohms;
T=temperature, ° C.;
A, B, C, D=empirically determined constants.

9. A method of continuously determining and monitoring watercut in a production fluid flowing through a pipeline from an oil reservoir, the flowing production fluid comprising oil, water and gas, the method comprising:

a. providing an impedance sensor unit and a temperature sensor at a fixed location in the pipeline for continuously measuring impedance values and temperature of the flowing production fluid in the pipeline, wherein the impedance sensor unit comprising at least one current electrode that is coupled to a first amplifier, at least one voltage electrode that is coupled to the first amplifier, an analog to digital converter (ADC) that is coupled to the first amplifier, a microprocessor; wherein the microprocessor includes a plurality of terminals, a first terminal that is coupled to the ADC and a second terminal that is coupled to a frequency generator; wherein a terminal of the frequency generator is coupled to a second amplifier and the second amplifier is coupled to the at least one current electrodes;

b. continuously measuring the impedance value and temperature of the flowing production fluid at the fixed location in the pipeline;

c. removing a sample of the production fluid during a shutdown of the fluid flow through the pipeline proximate the fixed location in the pipeline to determine a watercut value of the sample;

d. determining a correlation formula of the watercut value of the sample with the measured impedance value and temperature of the flowing production fluid at the fixed location at the time of obtaining the sample;

e. programming a computer with the correlation formula to provide a programmed computer to calculate the watercut of the flowing production fluid from impedance values inputted into the computer;

f. Subsequently inputting into the programmed computer the continuously measured impedance values and temperature to continuously calculate the watercut value of the flowing production fluid at the fixed location to thereby continuously determine the watercut of the flowing production fluid at the fixed location.

10. The method of claim 9, wherein the correlation formula is:

$$W = A \times |Z| + B \times |Z| \times T + C/T + D, \text{ where}$$

W=watercut,
|Z|=amplitude of complex impedance, ohms;
T=temperature, ° C.;
A, B, C, D=empirically determined constants.

11. The method of claim 9, further comprising repeating steps c., d., e., and f.

12. The method of claim 9, wherein the step of continuously measuring the impedance value and temperature of the flowing production fluid at the fixed location in the pipeline is performed at a fixed frequency of voltage.

13. A system for continuously determining and monitoring watercut in a production fluid flowing through a pipeline from an oil reservoir, the flowing production fluid comprising oil, water and gas, the system comprising:

a. an impedance sensor unit at a fixed location in the pipeline having electrodes in the flowing production fluid, wherein the impedance sensor continuously measures impedance values of the flowing production fluid in the pipeline, wherein the impedance sensor unit comprising at least one current electrode that is coupled to a first amplifier, at least one voltage electrode that is coupled to the first amplifier, an analog to digital converter (ADC) that is coupled to the first amplifier, a microprocessor; wherein the microprocessor includes a plurality of terminals, a first terminal that is coupled to the ADC and a second terminal that is coupled to a frequency generator; wherein a terminal of the frequency generator is coupled to a second amplifier and the second amplifier is coupled to the at least one current electrodes;

b. a temperature sensor at the fixed location in the pipeline, wherein the sensor continuously measures temperature of the flowing production fluid in the pipeline;

c. a programmed computer, wherein the computer is programmed with a correlation formula correlating the continuously measured impedance value and temperature of the flowing production fluid with the watercut of such flowing production fluid;

d. a means for inputting the continuously generated impedance values and temperatures of the flowing production fluids from the sensors to the programmed computer for calculating the continuous watercut of the flowing production fluid at the fixed location and displaying such watercut on a display of the programmed computer.

14. The system of claim 13, wherein the impedance sensor and temperature sensor are combined into one unitary sensor unit.

15. The system of claim 13, wherein the correlation formula is:

$$W = A \times |Z| + B \times |Z| \times T + C/T + D, \text{ where}$$

W=watercut,
|Z|=amplitude of complex impedance, ohms;
T=temperature, ° C.;
A, B, C, D=empirically determined constants.

16. A sensor unit for continuously determining and monitoring watercut in a production fluid flowing through a pipeline from an oil reservoir, the sensor unit comprising:

a. an impedance sensor unit for measuring an impedance value of the flowing production fluid, wherein the impedance sensor unit comprising at least one current electrode that is coupled to a first amplifier, at least one voltage electrode that is coupled to the first amplifier, an analog to digital converter (ADC) that is coupled to the first amplifier, a microprocessor; wherein the microprocessor includes a plurality of terminals, a first terminal that is coupled to the ADC and a second terminal that is coupled to a frequency generator; wherein a terminal of the frequency generator is coupled to a second amplifier and the second amplifier is coupled to the at least one current electrodes;

b. A temperature sensor unit for measuring a temperature value in the flowing production fluid;

c. A means for mounting the sensory unit in the pipeline wherein the impedance sensor unit and temperature sensor unit continuously measure the impedance value and temperature value of the flowing production fluid;

d. A means for communicating the continuously measured impedance value and temperature value to a programmed computer for calculating the continuous watercut of the flowing production fluid and displaying such watercut on a display of the programmed computer.

* * * * *